United States Patent
McLeod et al.

[11] Patent Number: 6,126,652
[45] Date of Patent: Oct. 3, 2000

[54] CATHETER BALLOON REFOLDING TOOL AND METHOD OF USE

[75] Inventors: Scot M. McLeod, San Diego; Michelle E. Fourmont, Carlsbad, both of Calif.

[73] Assignee: Medtronic Inc., Minneapolis, Minn.

[21] Appl. No.: 09/149,897

[22] Filed: Sep. 8, 1998

[51] Int. Cl.$^7$ ................................................. A61B 17/00
[52] U.S. Cl. ................................................................ 606/1
[58] Field of Search ........................... 604/99, 915, 96; 606/116, 1

[56] References Cited

U.S. PATENT DOCUMENTS

| | | | |
|---|---|---|---|
| 4,444,186 | 4/1984 | Wolvek et al. | 128/325 |
| 4,540,404 | 9/1985 | Wolvek | 604/96 |
| 4,601,713 | 7/1986 | Fuqua | 604/280 |
| 4,681,092 | 7/1987 | Cho et al. | 128/1 D |
| 4,710,181 | 12/1987 | Fuqua | 604/280 |
| 4,738,666 | 4/1988 | Fuqua | 604/280 |
| 4,901,707 | 2/1990 | Schiff | 128/1 D |
| 5,015,230 | 5/1991 | Martin et al. | 604/96 |
| 5,053,007 | 10/1991 | Euteneuer | 604/96 |
| 5,066,298 | 11/1991 | Hess | 606/194 |
| 5,087,246 | 2/1992 | Smith | 604/96 |
| 5,137,512 | 8/1992 | Burns et al. | 604/96 |
| 5,147,302 | 9/1992 | Euteneuer et al. | 604/96 |
| 5,163,989 | 11/1992 | Campbell et al. | 65/110 |
| 5,209,799 | 5/1993 | Vigil | 156/156 |
| 5,226,887 | 7/1993 | Farr et al. | 604/96 |
| 5,295,995 | 3/1994 | Kleiman | 606/194 |
| 5,318,587 | 6/1994 | Davey | 606/194 |
| 5,342,307 | 8/1994 | Euteneuer et al. | 604/103 |
| 5,350,361 | 9/1994 | Tsukashima et al. | 604/96 |
| 5,352,236 | 10/1994 | Jung et al. | 606/194 |
| 5,425,710 | 6/1995 | Khair et al. | 604/96 |
| 5,456,666 | 10/1995 | Campbell et al. | 604/96 |
| 5,458,572 | 10/1995 | Campbell et al. | 604/96 |
| 5,478,319 | 12/1995 | Campbell et al. | 604/96 |
| 5,549,552 | 8/1996 | Peters et al. | 604/96 |
| 5,690,613 | 11/1997 | Verbeek | 604/103 |
| 5,843,027 | 12/1998 | Stone et al. | 604/53 |

*Primary Examiner*—Linda C. M. Dvorak
*Assistant Examiner*—Jocelyn Debra Ram

[57] ABSTRACT

A refolding tool, tool system, and method of use for refolding the flaps of the inflatable balloon of a medical balloon catheter, particularly a dilatation balloon catheter for use in a percutaneous transluminal coronary angioplasty (PTCA) procedure, after it has been inflated and deflated or released from a balloon protector. The refolding tool is formed with a refolding tool body having a first tool end surface and preferably with a plurality of second tool end surfaces and a like plurality of refolding lumens extending from the first tool end surface to a respective one of the second tool end surfaces. Each refolding lumen has a unique refolding lumen length and lumen diameter exceeding the catheter body diameter. An initial refolding lumen of the refolding tool has an initial refolding lumen diameter that exceeds the specified refolded diameter and is sized to accommodate advancement of the balloon through the initial refolding lumen to refold the balloon to an initial refolded balloon diameter exceeding the specified refolded diameter. A final refolding lumen of the refolding tool has a final refolding lumen diameter that is smaller in diameter than the initial refolding lumen diameter and is sized to refold the initial refolded balloon diameter to the specified refolded diameter upon advancement of the balloon through the final refolding lumen to refold the balloon to substantially the specified refolded diameter. For balloon catheters having a balloon catheter lumen, the tool system comprises a support stylet that is advanced from the balloon catheter distal end through the catheter distal segment to stiffen the catheter distal segment during the refolding procedure.

35 Claims, 4 Drawing Sheets

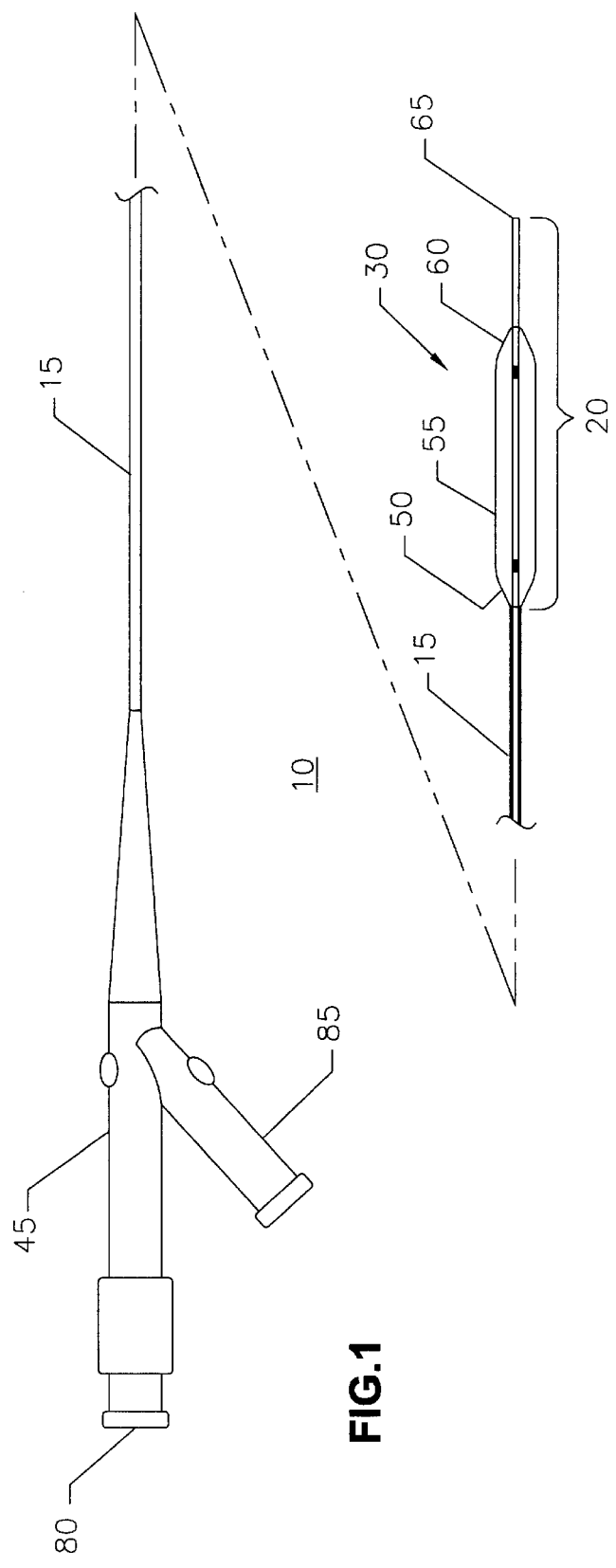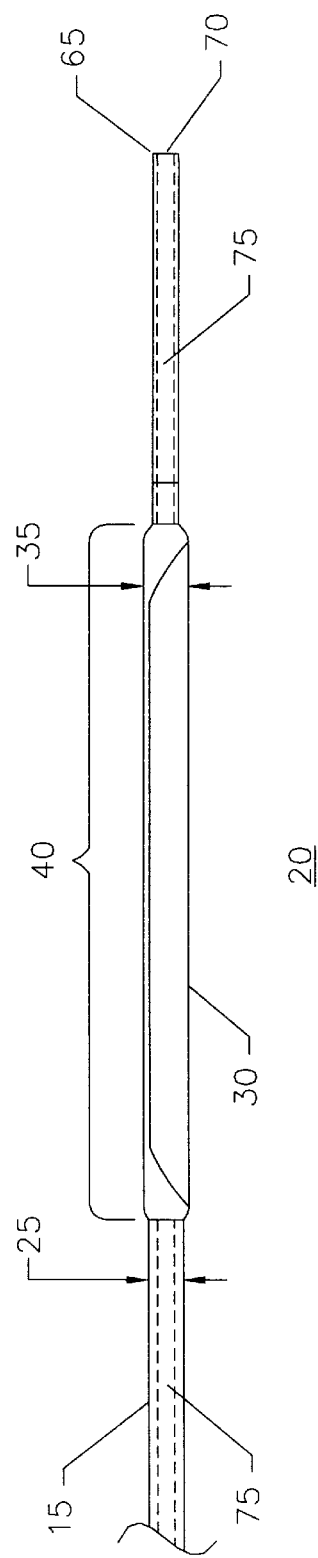
FIG.1
FIG.2

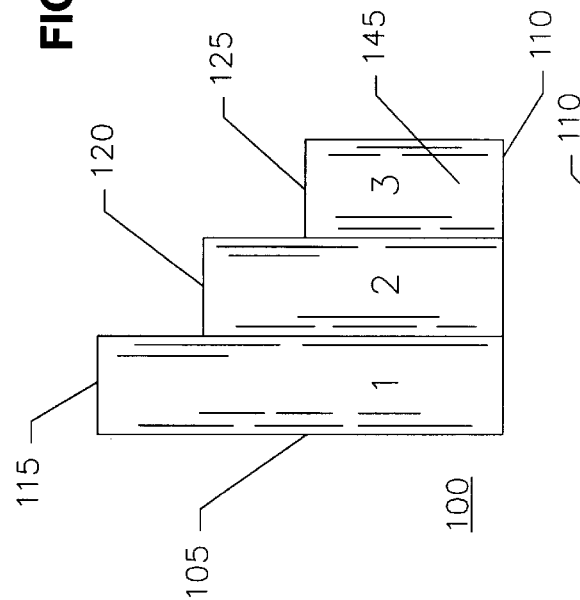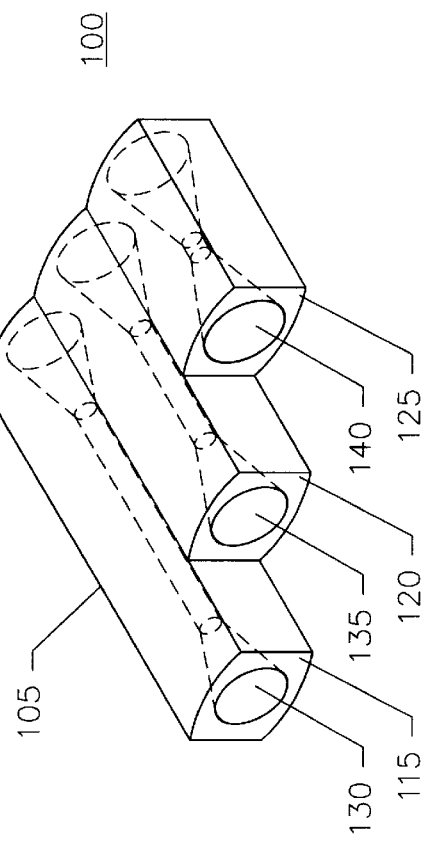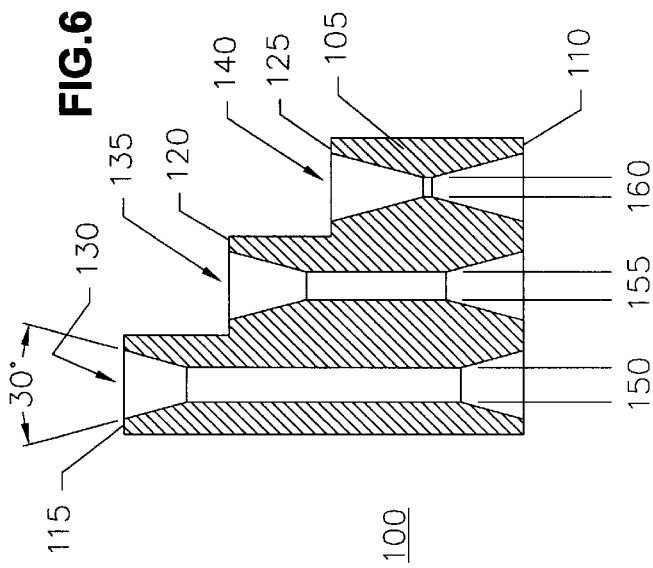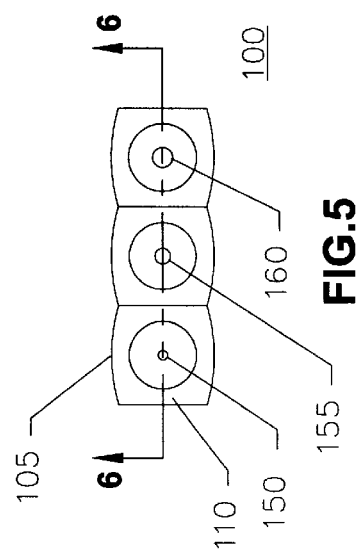

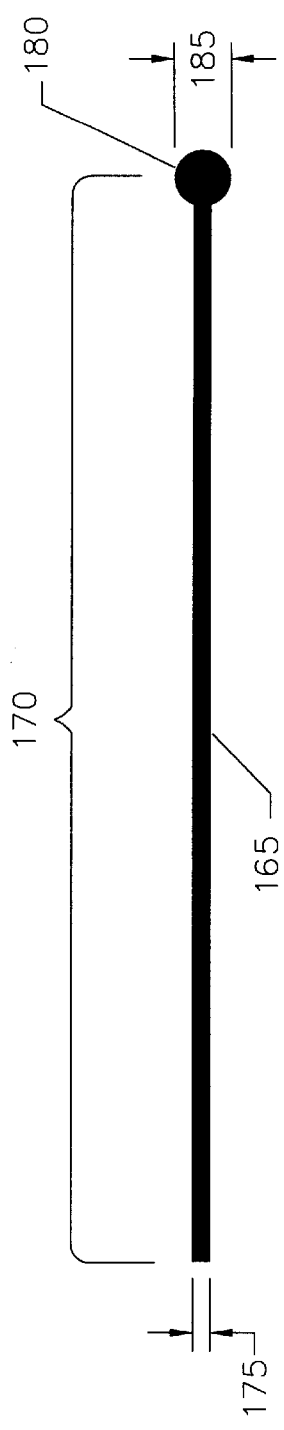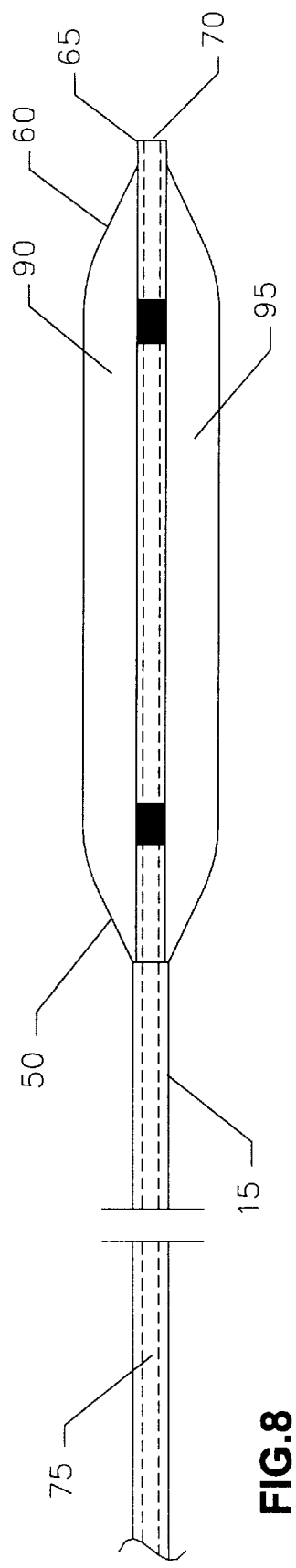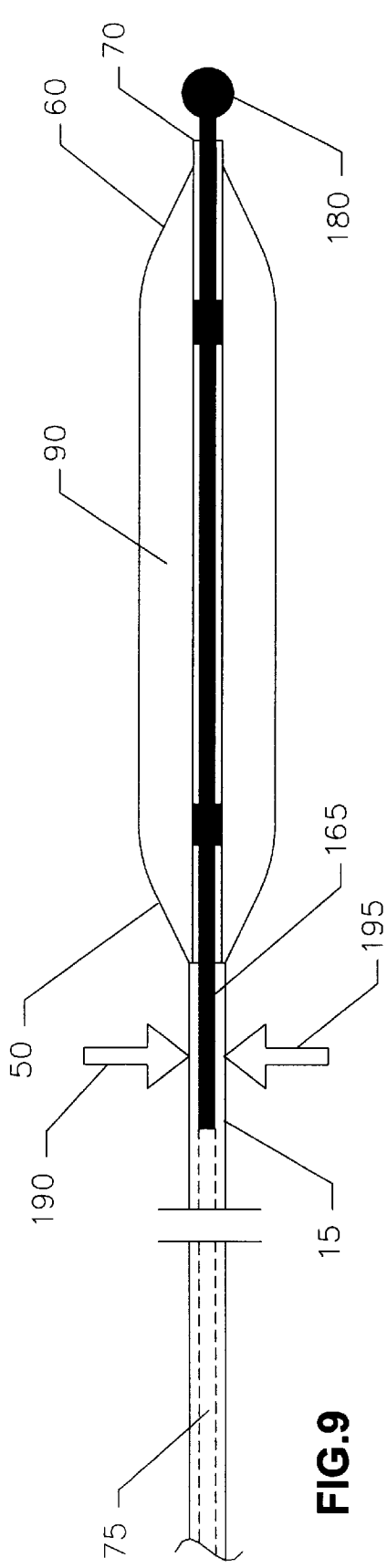

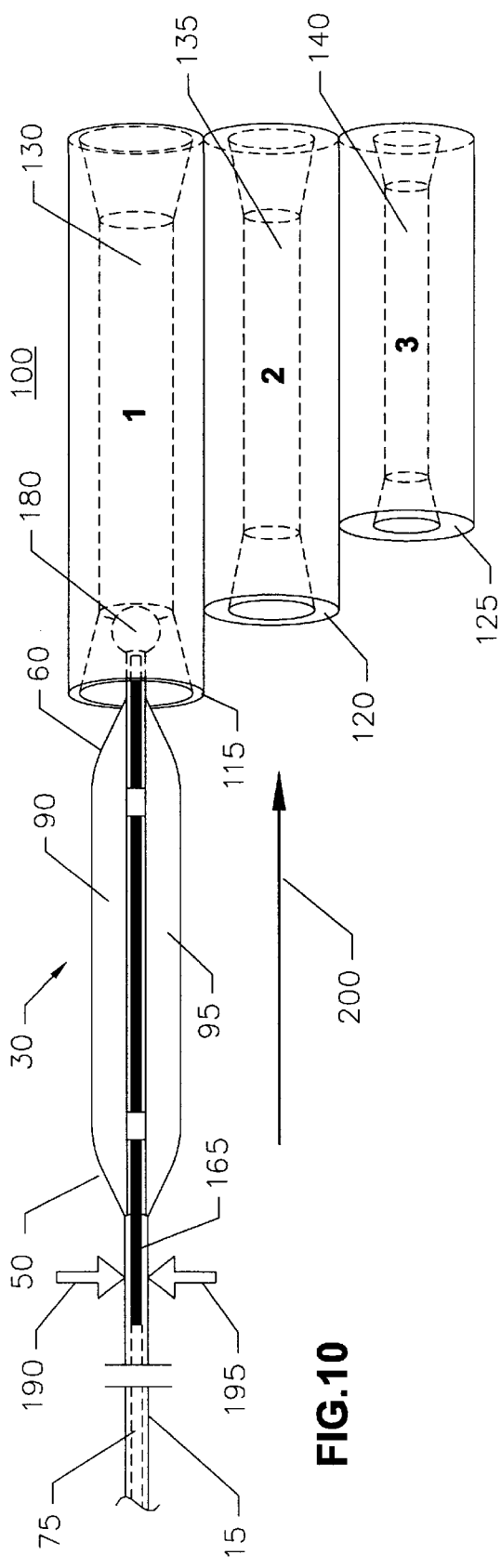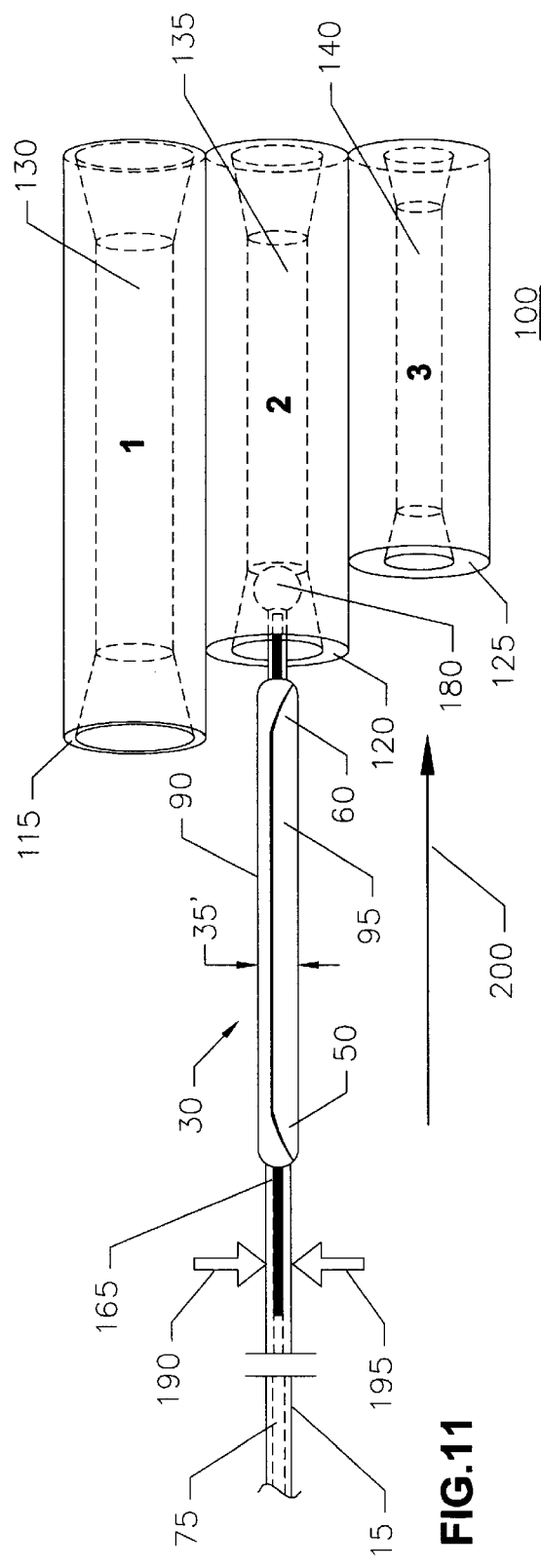

CATHETER BALLOON REFOLDING TOOL AND METHOD OF USE

FIELD OF THE INVENTION

The present invention relates to a refolding tool, tool system, and method of use for refolding the flaps of the inflatable balloon of a medical balloon catheter, particularly a dilatation balloon catheter for use in a percutaneous transluminal coronary angioplasty (PTCA) procedure, after it has been inflated and deflated or released from a balloon protector.

BACKGROUND OF THE INVENTION

Medical balloon catheters are tube-like medical instruments that are inserted into a body cavity, tract or duct or blood vessel for location of a deflated balloon at a vascular site and remote inflation at the site for diagnostic or therapeutic reasons. Balloon angioplasty catheters are widely used in angioplasty procedures for efficiently and effectively opening stenoses in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to re-establish acceptable blood flow through the artery.

One important characteristic of a dilatation catheter used for angioplasty is its profile, i.e., the outer diameter of the distal end portion of the balloon. Considerable effort has been spent in developing low-profile dilatation balloon catheters by minimizing the dimensions of the core or inner tube which extends through the balloon to its distal end, and by reducing wall thickness, to the extent possible, of the balloon itself.

Another important consideration is the outer diameter of the catheter in its deflated condition. This outer diameter affects the ease and ability of the dilatation catheter to pass through an introducer or guide catheter and through the coronary arteries leading to the stenosis to be opened.

The angioplasty balloon material, thickness, and length are selected to provide an inelastic balloon capable of being inflated to a predetermined diameter and length and to exert relatively high pressure against an occlusion of a blood vessel wall to expand it or to fracture it. Because the balloon material is not elastic, it has a fixed inflated diameter and it cannot deflate to a smaller diameter than its inflated diameter. Thus in the deflated state, the balloon material collapses upon itself forming flaps or wings that must be folded or wrapped around the balloon catheter to allow it to be withdrawn from the patient's vascular system after it is used. And, before it is used, the balloon catheter has to be folded or wrapped about the balloon catheter body to fit within and pass through the guide catheter lumen. When inflation fluid is applied to the deflated balloon, it causes the balloon flaps to unwrap so that the balloon can inflate to its fully inflated condition. Such balloon catheters are disclosed, for example, in commonly assigned U.S. Pat. Nos. 5,690,613 to Verbeek and 5,350,361 to Tsukashima et al., both incorporated herein by reference.

Various techniques or balloon constructions are employed order to encourage the balloon to fold about the balloon catheter body in a uniform manner when it is evacuated in two or three or four or more flaps or wings of the same size. One approach has been to construct the balloon of a cylinder of material, e.g., polyethylene, that is uniform about its circumference but can be heat set after it is wrapped or folded to form curved, overlapping flaps or wings extending from fold lines in a manner described further below. Another approach has been taken to fabricate the balloon itself with fold line structures and flap shapes, particularly for use with balloons formed of stronger polyesters e.g. polyethylene terepthalate (PET). These techniques are set forth, for example in U.S. Pat. Nos. 5,053,007, 5,147,302 and 5,342,307 to Euteneuer, U.S. Pat. No. 5,087,246 to Smith, U.S. Pat. No. 5,147,302 to Euteneuer et al., U.S. Pat. Nos. 5,163,989, 5,456,666, and 5,458,572 to Campbell et al., U.S. Pat. No. 5,209,799 to Vigil, U.S. Pat. No. 5,226,887 to Farr et al., and U.S. Pat. No. 5,318,587 to Davey and in commonly assigned U.S. Pat. No. 5,350,361 to Tsukashima et al., all incorporated herein by reference. In the Euteneuer '107, '302 and '307 patents, "tri-fold" balloons are formed by folding the balloon along fold lines of the balloon located 120° apart around the balloon circumference and then subjecting the folded balloon to an initial heat treatment to set the fold lines. In the Tsukashima '361 patent, the tri-fold balloons are folded in a similar manner and then the fold lines of the balloon located 120° apart around the balloon circumference are subjected to heat treatment to set the fold lines. The remaining cited patents disclose other fold line structures for inelastic medical balloons including angioplasty balloons, intra-aortic balloons and esophageal dilatation balloons.

In the prior art, it has been common to use a balloon protector in conjunction with such balloon dilatation catheters. A balloon protector serves at least two important functions. First, it protects the balloon and distal tip of the catheter from possible damage during shipping and handling before it is removed. Second, the balloon protector keeps the balloon tightly wrapped in its deflated condition to minimize the outer diameter of the balloon in its deflated state.

A balloon protector is typically applied to the distal end portion of the catheter prior to sterilization of the catheter. The sterilization process can involve exposing the catheter, with the balloon protector in place, to an elevated temperature for a period of time. With certain balloon materials, e.g., polyethylene (PE), the sterilization process will advantageously cause the balloon to be heat set in the folded or wrapped configuration in which it is held by the balloon protector. As a result, when the balloon protector is later removed, the balloon remains in this tightly wrapped or folded configuration.

The heat setting of a balloon has the further advantage that when the balloon is inflated and then deflated, as it may be several times during an angioplasty procedure, the application of negative pressure during deflation will cause the balloon to return fairly closely to its tightly wrapped heat set configuration. This greatly facilitates the removal of the catheter after the procedure has been performed.

Various types and configurations of balloon protectors have been shown in the prior art, for example, in the above-incorporated Euteneuer '107, '302 and '307 patents and in commonly assigned U.S. Pat. Nos. 5,352,356 to Jung et al. and 5,425,710 to Khair et al., U.S. Pat. No. 4,901,707 to Schiff, U.S. Pat. Nos. 4,738,666 and 4,710,181 to Fuqua, U.S. Pat. No. 5,066,298 to Hess, U.S. Pat. No. 5,137,512 to Burns, and U.S. Pat. No. 4,540,404 to Wolvek, all incorporated herein by reference.

The above-incorporated Fuqua '666 and '181 patents propose a catheter protector comprising a hollow cylindrical sheath. The Fuqua sheath covers the entire length of the catheter, and is removed by pulling it off of the proximal end of the catheter. Fuqua also proposes providing perforations in the sheath for facilitating its removal. A similar arrangement is proposed in the above-incorporated Wolvek '404 patent, in which a sheath is slidably disposed over a substantial section of a catheter body, covering the balloon disposed at the distal end of the catheter body. The sheath and catheter assembly are advanced into the patient's vascular system until the distal balloon end is positioned in the area to be dilated. The sheath is long enough that its proximal end remains exposed outside of the patient, such that the sheath may be withdrawn along the catheter body until the balloon is uncovered. Then, the dilatation procedure can be performed.

The above-incorporated Euteneuer '007, '302 and '307 patents also disclose use of a compression protector employing an inner sleeve applied over a deflated balloon, an outer sleeve applied over the inner sleeve, and a compression housing for compressing the outer sleeve radially in on the inner sleeve, thus compressing the inner sleeve radially in on the balloon. With the balloon thus compressed within the Euteneuer protectors, the catheter is then sterilized at an elevated temperature. The inner and outer sleeves are formed of materials which exhibit heat-shrink qualities such that the heat treatment causes the balloon to be further compressed to a smaller outer diameter along the previously formed fold lines. The Euteneuer protectors are removed just prior to introduction of the catheter into the patient, with the balloon retaining its compressed form as a result of the heat treatment.

The above-incorporated Hess '298 patent proposes protecting a catheter's balloon by wrapping the balloon with tape in an overlapping fashion. In a manner similar to that proposed in the Euteneuer patents, the Hess '298 balloon is subjected to heat treatment after being wrapped, in order to further compress the balloon and affect a heat-setting of the balloon in its compressed condition.

In the above-incorporated Burns '512 patent, a multi-segment balloon protector is disclosed formed of two or more Teflon® PTFE tubes, usually axially aligned and of different diameters. Less force is required to apply the protectors, resulting in a lower chance of tearing the balloon when the protector is applied.

The above-incorporated, commonly assigned '236, and '710 patents disclose improved tubular sleeve balloon protectors that receive the folded or wrapped balloon within elongated sleeve lumens without requiring twisting of the balloon in order to advance it into the sleeve lumens. A split inner sleeve of lubricious material is employed in the '236 patent, and a coating of lubricious material, particularly parylene, on the sleeve lumen surface is disclosed in the '710 patent. The balloon protector shrinks during heat sterilization to tightly hold the balloon in the folded condition and heat set the folds of the balloon.

The use of a rigid balloon protector formed of two elongated half sections that are fitted over to enclose a folded intra-aortic balloon having an integral stylet formed therein and then attached together is disclosed in the above-incorporated Schiff '707 patent. The initial wrapping of the balloon about the integral stylet and catheter body extending through the balloon is apparently accomplished manually before the wrapped balloon is placed into the tubular opening of the elongated half sections.

While these techniques have aided in forming inelastic medical balloons that tend to refold or rewrap their flaps about fold lines, it is still necessary at times to rewrap the balloons after they have been removed from the balloon protectors and are outside of the patient's body.

The necessary tightness of the winding and reduction of the folded balloon diameter cannot be achieved readily by simply manually twisting the balloon folds around one another. Moreover, manual twisting of the balloon can damage it. In order to overcome this problem, it has been customary to provide a refolding or rewrapping tool kit with the balloon angioplasty catheters that the physician employs to tightly wind the balloon flaps around one another. These kits include the Sci-Med® Wrap-It™ refolding tool included with the Sci-Med® NC Bandit™ PTCA catheter, the CDV™ balloon refolding tool sold with the CVD FACT™ PTCA catheter by the assignee of the present invention, and the ACS® balloon sheath. The ACS® balloon sheath constitutes a simple protector tube having a flared, conical end opening that is used as a balloon protector as described above and which is stated to be used as a "regrooming" sheath. The WRAP-It™ refolding tool is a plastic tubular member having a tool lumen extending therethrough an a flared conical end and a relatively stiff, short mandrel or stylet having an eyehook at one end. In use, the stylet is inserted through the tool lumen so that the straight stylet end extends from the flared lumen end opening. The straight stylet end is inserted into the distal end opening of the PTCA catheter lumen, and the user then pinches and rolls the balloon between the fingers to advance it over the sylet and through the tool lumen to roll the balloon flaps into the spiral. Several passes may be required because the tool only comes in one tool lumen size for all balloon sizes. The CDV™ balloon refolding tool also comprises a tool and wire stylet of this type except that it is provided in different tool lumen sizes to receive different sized balloons and in that the stylet eye hook end is fixed in the tool lumen at the straight end.

The use of rewrapping or refolding tools for rewrapping flaps of inflexible intra-aortic balloons has also been disclosed in U.S. Pat. No. 4,444,186 to Wolvek et al. and in U.S. Pat. No. 4,681,092 to Cho. In the Wolvek '186 patent, a wrapping guide is disclosed that aids in spirally wrapping an intra-aortic balloon immediately before it is inserted into and through the guide catheter lumen. In the Cho '092 patent, a several part wrapping apparatus for wrapping a bi-fold, intra-aortic balloon is disclosed. Two half sections that fit together receive the deflated balloon and a shoe and biasing member in an elongated channel that has channel extensions that receive the two deflated flaps. After assembly, the catheter body is twisted to rotate the balloon and pull the flaps from the outlying channels and wrap them around one another and the catheter body. This twisting and pulling motion can cause damage to fragile balloon structures and is awkward.

Notwithstanding such proposals, however, there is perceived by the inventors to be a continuing need for improved balloon rewrapping or refolding tool and method for rewrapping balloon flaps of medical balloon catheters.

SUMMARY OF THE INVENTION

It is therefore an object of the present invention to provide an improved balloon rewrapping or refolding tool and method for rewrapping balloon flaps of medical balloon catheters that is simple to use while achieving a tight wrapping of the balloon flaps into a small diameter.

It is a further object of the present invention to provide such an improved balloon rewrapping or refolding tool and method for rewrapping balloon flaps of medical balloon catheters that does not involve twisting the balloon catheter body or balloon flaps and avoids damaging the balloon.

These and other objects of the invention are realized in a balloon refolding tool and tool system and method of use for refolding a balloon of a balloon catheter of the type having an elongated catheter body having a catheter body diameter. An inflatable and deflatable balloon of a predetermined balloon length is mounted to a distal segment of the catheter body and can be wrapped or folded along balloon fold lines to a specified refolded diameter correlated with the catheter body diameter and sufficient to be advanced through a patient's vascular system by itself or within a guide catheter lumen to a desired vascular site.

The refolding tool is formed with a refolding tool body having a first tool end surface and preferably with a plurality of second tool end surfaces and a like plurality of refolding lumens extending from the first tool end surface to a respective one of the second tool end surfaces so that each refolding lumen has a unique refolding lumen length, the plurality of refolding lumens having differing refolding lumen diameters all exceeding the catheter body diameter. An initial refolding lumen of the refolding tool has an initial refolding lumen diameter that exceeds the specified refolded diameter and is sized to accommodate advancement of the balloon through the initial refolding lumen to refold the balloon to an initial refolded balloon diameter exceeding the specified refolded diameter. A final refolding lumen of the refolding tool has a final refolding lumen diameter that is smaller in diameter than the initial refolding lumen diameter and is sized to refold the initial refolded balloon diameter to the specified refolded diameter upon advancement of the balloon through the final refolding lumen to refold the balloon to substantially the specified refolded diameter. Preferably, the refolding tool contains at least one intermediate refolding lumen that has an intermediate refolding lumen diameter that is sized intermediate the initial and final refolding diameters.

In the method of use of the refolding tool, the deflated balloon is successively advanced and withdrawn through at least two of the refolding lumens, starting with the largest diameter initial refolding lumen appropriate to the balloon catheter body diameter and ending with the final diameter refolding lumen appropriate to the balloon catheter body diameter. The balloon catheter body is grasped proximal to the balloon flaps and is advanced and withdrawn straight through the refolding lumens without twisting of the balloon. The balloon flaps fold along their fold lines as the balloon is advanced first through the initial refolding lumen. Then, the loosely folded balloon flaps are folded tighter as the balloon is advanced through the final refolding lumen (and optionally through an intermediate refolding lumen). The balloon catheter lumen is preferably supported through the length of the balloon catheter distal segment and the point where the balloon catheter body is grasped if the balloon catheter is formed with a balloon catheter lumen extending distally and proximally to the balloon.

In this context, a refolding tool system combines the refolding tool with support means adapted to be assembled as an assembly with the catheter body for supporting the catheter body lumen in at least the distal segment of the catheter body from collapse when it is grasped to advance or withdraw the balloon straight through the refolding lumens. The support means preferably comprises a stylet having a proximal end that is insertable into the distal lumen end opening of the balloon catheter lumen and extends proximally to the balloon and a distal end having an enlarged ball tip that abuts the distal end opening and does not enter it.

The preferred embodiment method of refolding the flaps preferably comprises the steps of: inserting the proximal stylet end of the support stylet into the distal lumen end opening so that the ball tip bears against but does not enter the distal lumen end opening or expand the distal lumen end opening diameter and the stylet extends within the balloon catheter lumen to the proximal stylet end at a location proximal to the balloon to stiffen and support the distal segment of the catheter body; manually grasping the catheter body at the location that the inserted stylet extends to proximal to the balloon; inserting the stylet ball tip into an initial refolding lumen of the refolding tool that exceeds the specified refolded diameter and the stylet ball tip diameter; advancing and withdrawing the assembly of the support stylet and balloon catheter distal segment through the initial selected refolding lumen, whereby the flaps of the balloon are refolded to an initial refolded balloon diameter exceeding the specified refolded diameter; inserting the stylet ball tip into the appropriate final refolding lumen of the refolding tool that exceeds the specified refolded diameter and the stylet ball tip diameter; and advancing and withdrawing the assembly of the support stylet and balloon catheter distal segment through the selected final refolding lumen, whereby the flaps of the balloon are refolded to the specified final refolded balloon diameter.

In certain instances, it may be desirable to employ one or more intermediate diameter refolding lumen of the refolding tool that exceeds the specified refolded diameter after withdrawing the assembly from the selected initial refolding lumen, adding the steps of: inserting the stylet ball tip into the appropriate intermediate refolding lumen of the refolding tool that exceeds the specified refolded diameter and the stylet ball tip diameter; and advancing and withdrawing the assembly of the support stylet and balloon catheter distal segment through the selected intermediate refolding lumen, whereby the flaps of the balloon are refolded to an intermediate refolded balloon diameter exceeding the specified refolded diameter.

The refolding lumens of the tool and the stylet diameter and length are preferably sized to accomplish the refolding of a range of balloon catheter body and balloon diameters and distal segment lengths, respectively. The initial and final refolding lumens, and any intermediate refolding lumen(s), of the refolding tool can be selected to receive and refold the balloons in the size range. Specific stylets may be provided that have stylet diameters and lengths appropriate to be received in balloon catheter lumens and support the distal segment length.

The use of the tool and the tool system in accordance with the above described refolding methods is simple and rapid and does not unduly stress the balloon flaps. Damage to the balloons is minimized due to the straight advancement and withdrawal of the balloon through the refolding lumens. Moreover, one tool can be used for a wide range of balloon sizes through selective use of at least two of the refolding lumens.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 1 is a plan view of a typical medical balloon catheter having an inelastic and non-compliant balloon which can be refolded in a deflated state in a flap or plurality of overlapping flaps about the catheter body in a distal segment thereof;

FIG. 2 is an expanded view of the distal segment of the balloon catheter with the balloon flaps wrapped or folded about the catheter body to a specified diameter;

FIG. 3 is perspective view of a preferred embodiment of the balloon refolding tool of the present invention;

FIG. 4 is plan view of the preferred embodiment of the balloon refolding tool of FIG. 3;

FIG. 5 is an end view of the preferred embodiment of the balloon refolding tool of FIG. 3;

FIG. 6 is a cross-section view of the preferred embodiment of the balloon refolding tool of FIG. 3 taken along lines 6—6 of FIG. 5;

FIG. 7 is a plan view of a support stylet for supporting the catheter body of hollow lumen medical balloon catheters from collapse during use of the refolding tool of FIGS. 3–6;

FIG. 8 is a schematic illustration of the distal segment of a hollow lumen medical balloon catheter of FIG. 1 and the deflated balloon flaps;

FIG. 9 is a plan view of the support stylet of FIG. 7 inserted through the distal lumen end opening of the balloon catheter lumen and extending proximally to the balloon flaps to support the balloon catheter body in the use of the refolding tool of FIGS. 3–6 illustrated in FIGS. 10 and 11;

FIG. 10 is an illustration of the insertion of the assembly of the support stylet and distal segment of the balloon catheter into a selected initial refolding lumen of the refolding tool; and FIG. 11 is an illustration of the insertion of the assembly of the support stylet and distal segment of the balloon catheter with the balloon flaps, folded to an initial balloon diameter after withdrawal from the selected initial refolding lumen of FIG. 10, into a selected final refolding lumen of the refolding tool resulting in the folded balloon of FIG. 2.

SUMMARY OF THE INVENTION

FIG. 1 is a plan view of a typical medical balloon catheter 10 having an inelastic and non-compliant balloon 30, depicted in an inflated state, which can be refolded in a deflated state in a flap or plurality of flaps about the catheter body 15 in a distal segment 20 thereof. The balloon catheter body 15 has a catheter body diameter 25 in the distal segment 20 that, together with the folded flaps of the balloon 30 defines a specified refolded diameter 35 which is shown in the enlarged view of FIG. 2. The balloon 30 extends outward of the catheter body 15 and has a predetermined balloon length 40 along the distal segment 20. When inflated as shown in FIG. 1, the balloon 30 has a proximal balloon portion 50 that increases in diameter distally, an intermediate balloon portion 55 that is substantially cylindrical, and a distal balloon portion 60 that decreases in diameter distally.

In the illustrated embodiment of the balloon catheter 10, the catheter body 15 is formed with two lumens that extend through its length between a hub 45 coupled at the catheter body proximal end and the interior of the balloon 20 and a distal catheter lumen end opening 70 at the catheter distal end 65. The latter catheter lumen 75 extends through the proximal hub 45 to a proximal catheter lumen end opening 80 and is adapted to receive a guidewire (not shown) during the over-the-wire (OTW) advancement of the balloon catheter 10. The other lumen (not illustrated) extends through the catheter body 15 between the side port extension 85 and the interior of the balloon 30 and is used to inflate and deflate the balloon 30 in a manner well known in the art.

The illustrated balloon catheter preferably comprises a PTCA catheter that is intended to be advanced to the site of an occlusion in a blood vessel with the balloon 30 deflated and the balloon flaps wrapped or folded about one another and the underlying balloon catheter body as shown in FIG. 2. The advancement is effected over a previously advanced guidewire (not shown) extending through the balloon catheter lumen 75 by itself or within a guide catheter lumen to a desired vascular site in a manner well known in the art, and unimportant to the practice of the present invention. The balloon catheter 10 preferably takes the form of the Millenia™ PTCA catheters sold by the assignee of the present invention and those balloon catheters described in commonly assigned U.S. Pat. No. 5,690,613 to Verbook, incorporated by reference. The balloon catheter 10 is formed of materials described in the Verbook '613 patent, particularly the materials specified therein for the catheter body 15 and balloon 30. The relatively elongated proximal segment of the catheter body 15 is formed of a relatively stiff, reinforced tubing material, and the shorter distal segment 20 is formed of 50% HDPE/50% LDPE. The material of the balloon 30 is inelastic and non-compliant that is suitable for high pressures about 12 atm to 16 atm, e.g., PET or Nylon or PET blend film of a thickness of about 0.020 mm.

The balloon 30 is heat treated in the manner described above and normally surrounded by a protector of the type described in the above-incorporated Jung '236 or Khair '710 patents before it is first used in a PTCA procedure. The balloon 30 preferably is wrapped in a bi-fold configuration or a tri-fold configuration as shown in the above-incorporated Tsukashima '361 patent, but it can be folded with even more folds or flaps. The illustrated two deflated flaps 90 and 95 extend outward of the catheter body 15 from 180° locations along the sides of the catheter body 15 along the distal segment 20.

When the balloon 30 is inflated to the substantially cylindrical shape, it has a fixed diameter in the intermediate balloon portion 55, and such PTCA balloon catheters 10 are usually provided with a range of inflated balloon diameters of 1.50 mm to 4.00 mm, for example. The catheter body diameter 25 in the distal segment 20 under the balloon 30 is, in this particular embodiment, about 0.584 mm. The deflated balloon flaps 90 and 95 of the 1.50 mm balloon wrap about the catheter body about 1 turns each and result in a specified folded or refolded balloon diameter 35 of about 0.762 mm. The deflated balloon flaps 90 and 95 of the 4.00 mm balloon wrap about the catheter body about 1 turns each and result in a specified folded or refolded balloon diameter 35 of about 1.35 mm.

In the course of a PTCA procedure, it may become necessary to inflate the balloon 30 and then deflate it and reposition it as described above. At this point, the balloon flaps 90 and 95 may loosely wrap about one another and assume an expanded folded balloon diameter which exceeds the specified refolded diameter 35. It may then be necessary to use the refolding tool system and method of the present invention to refold the balloon flaps 90 and 95 to the specified refolded balloon diameter 35.

The balloon refolding tool 100 of the present invention is shown in FIGS. 3–6, and a support stylet 165 that is preferably used with the refolding tool 100 is shown in FIG. 7 and described below. The support stylet 165 is intended to be used to support the catheter body 15 of such hollow lumen OTW medical balloon catheters from collapse during use of the refolding tool 100. However, it will be understood that the refolding tool 100 can be employed by itself without use of the support stylet 165 in the practice of the invention for refolding balloon catheter flaps that are formed over a more rigid catheter body or a catheter body that is formed with an integral guide wire or the like extending through the distal segment. The use of the refolding tool 100 will be explained in the context of the its use in refolding hollow lumen balloon catheter balloon flaps.

In FIGS. 3–6, the refolding tool 100 has a generally rectangular, box-shaped, refolding tool body 105 formed of a unitary, injection molded, piece of NOVACOR™ Styrene Methyl Methacrylate Copolymer plastic that extends between a first end surface 110 and preferably with a plurality, e.g. three, of second end surfaces 115, 120 and 125. A like plurality of refolding lumens 130, 135 and 140 extend from the first end surface 110 to a respective one of the second tool end surfaces 115,120 and 125. Each refolding lumen 130, 135 and 140 has a unique refolding lumen length and is identified by numerals "1", "2" and "3", respectively, molded on opposed major surfaces, e.g., surface 145, of the refolding tool body 105.

The refolding lumens 130, 135 and 140 have differing refolding lumen diameters 150,155 and 160, respectively, all exceeding the catheter body diameter 25 of the balloon catheter 10 that the refolding tool 100 is intended to be used with. The refolding lumen diameters 150,155 and 160 are selected with respect to the range of balloon diameters of and corresponding specified refolded balloon diameters 35 over a specified catheter body diameter. In respect to the specific catheter body diameter 25 and range of specified refold diameters identified above for the 1.50 to 4.00 mm balloon catheters, the refolding lumen diameters 150,155 and 160 are nominally 0.73, 0.63 and 0.53 inches, respectively. These refolding lumen diameters are selected so that at least one of the larger refolding lumens denoted "1" or "2" can be selected as an initial refolding lumen in the step illustrated in FIG. 10 and the next smaller refolding lumens denoted "2" or "3" can be selected as a final refolding lumen in the step illustrated in FIG. 11. For example, the largest refolding lumen denoted "1" and the next largest refolding lumen denoted "2" are preferably used as the initial and final refolding lumens to refold the deflated balloon flaps of the 3.00 mm to 4.00 mm balloons. Similarly, the next largest refolding lumen denoted "2" and the smallest refolding lumen denoted "1" are preferably used as the initial and final refolding lumens to refold the deflated flaps of the 1.50 mm to 2.75 mm balloons. It would also be possible to successively employ all three refolding lumens 130, 135 and 140 in appropriate cases to refold a balloon catheter.

The refolding lumens 130, 135 and 140 each have enlarged first end opening diameters in the first tool surface 110 and enlarged second end openings in the second tool surfaces that are enlarged from the respective refolding lumen diameters 150, 155 and 160. Conical, funnel shaped insertion surfaces are formed in the tool body 105 extending from the enlarged first and second end opening diameters to the refolding lumen diameters 150, 155, 160 for contacting and guiding the proximal or distal balloon portions 50 or 60 into the respective refolding lumen diameters 150, 155, 160. The conical, funnel shaped surfaces preferably are tapered at about 15° to the axis of the refolding lumens 130, 135, 140.

The support stylet 165 of FIG. 7 has a stylet length 170 that exceeds the predetermined balloon length 40 and the length of the distal segment 20 and a stylet diameter 175 that fits within the balloon catheter lumen 75. A ball tip 180 with a ball diameter 185 exceeding the diameter of the distal lumen end opening 70 is formed at the distal stylet end.

The proximal end of the support stylet 165 is intended to be inserted into the distal lumen end opening 70 shown in FIG. 8 and advanced proximally until the ball tip 180 bears against but does not enter the distal lumen end opening 70 or expand the distal lumen end opening diameter as shown in FIG. 9. The stylet 165 extends within the balloon catheter lumen 75 to the stylet proximal end at a location within the balloon catheter lumen proximal to the balloon flaps 90 and 95. The catheter body 15 can be manually grasped at a supported location of the catheter body 15 designated by pressure arrows 190 and 195 that the inserted stylet extends to.

FIG. 10 illustrates of the insertion of the assembly of the support stylet 165 and distal segment 20 of the balloon catheter 10 into a selected initial refolding lumen of the refolding tool 100 with the balloon flaps 90 and 95 extending outward of the balloon catheter body 15. In this case, the selected initial refolding lumen is the refolding lumen 130 denoted "1" on the tool surface overlying it. The physician manually grasps the catheter body 15 at the location denoted by the pressure arrows 190, 195 that the inserted stylet 165 extends to proximal to the balloon 30. Then, the stylet ball tip 180 is inserted into the enlarged second end opening of the initial refolding lumen 130 of the refolding tool 100 as depicted. Then, by applying smooth steady pressure and force in the direction of arrow 200, the assembly of the support stylet 165 and balloon catheter distal segment 20 is advanced through the initial selected refolding lumen 130 and then withdrawn therefrom. The flaps 90 and 95 of the balloon 30 are refolded to an initial refolded balloon diameter 35' exceeding the specified refolded balloon diameter 35 as shown in FIG. 11.

FIG. 11 is an illustration of the insertion of the assembly of the support stylet 165 and distal segment 20 of the balloon catheter 10 with the balloon flaps 90 and 95 folded to the initial balloon diameter 35', after withdrawal from the selected initial refolding lumen 130 of FIG. 10, into a selected final refolding lumen of the refolding tool 100 resulting in the refolded balloon diameter 35 of FIG. 2. In this case, the selected final refolding lumen is the next smaller refolding lumen 135 denoted "2" on the tool surface overlying it. The physician again manually grasps the catheter body 15 at the location denoted by the pressure arrows 190, 195 that the inserted stylet 165 extends to proximal to the balloon 30. Then, the stylet ball tip 180 is inserted into the enlarged second end opening of the final refolding lumen 135 of the refolding tool 100 as depicted. Then, by applying smooth steady pressure and force in the direction of arrow 200, the assembly of the support stylet 165 and balloon catheter distal segment 20 is advanced through the final selected refolding lumen 135 and then withdrawn therefrom. The flaps 90 and 95 of the balloon 30 are refolded to the specified refolded balloon diameter 35. The stylet 165 is then withdrawn from the balloon catheter lumen 75.

This same technique can be employed to refold smaller diameter balloons by employing the smaller refolding lumen 135 denoted "2" on the tool surface overlying it as the initial refolding lumen and then employing the smallest refolding lumen 140 denoted "3" on the tool surface as the final refolding lumen. And, as noted earlier, all three refolding lumens can be used in appropriate cases. In addition, the refolding tool 100 can be provided with additional refolding lumens if it is desirable to refold a wider range of balloon diameters.

The refolding tool 100 is provided with the stepped surfaces 115, 120, and 125 and the stepped down lengths of the successively smaller diameter refolding lumens 130, 135, and 140 and the numerals "1,", "2", and "3" enable the physician to readily identify the appropriate lumen. More importantly, the smaller diameter refolding lumens are shortened progressively to reduce friction between the balloon and the refolding lumen.

The balloon refolding method, tool and tool system of the present invention has been described above in the illustrative context of a hollow lumen PTCA catheter requiring stiffening and support by use of the support stylet 165. As noted at the outset, it will be understood that the refolding method and tool may be practiced and used to refold balloons of PTCA catheters constructed with crush resistant catheter bodies at the pressure arrows 190 and 195 and relatively stiff distal end segments that can be advanced in the direction of arrow 200 without such support.

It will also be understood that the balloon refolding method, tool and tool system of the present invention can be practiced and employed to refold catheter balloons of other medical balloon catheters having non-compliant, inelastic balloons, e.g., intra-aortic balloon catheters, esophageal balloon catheters, and the like.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

PARTS LIST FOR FIGS. 1–11 balloon catheter 10
catheter body 15
distal segment 20
catheter body diameter 25
balloon 30
specified refolded diameter 35
balloon length 40
proximal hub 45
proximal balloon portion 50
intermediate balloon portion 55
distal balloon portion 60
distal catheter lumen end opening 70
catheter lumen 75
proximal catheter lumen end opening 80
side port extension 85
bi-fold balloon flap 90
bi-fold balloon flap 95
refolding tool 100
refolding tool body 105
first tool end surface 110
second tool end surfaces 115,120 and 125
refolding lumens 130, 135 and 140
major tool surface 145,
refolding lumen diameters 150, 155, 160
support stylet 165
stylet length 170
stylet diameter 175
ball tip 180
ball tip diameter 185
pressure arrows, 190, 195
insertion direction 200

What is claimed is:

1. A refolding tool for refolding a balloon of a balloon catheter of the type having an elongated catheter body having a catheter body diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising:

a refolding tool body having a plurality of refolding lumens having differing refolding lumen diameters all exceeding the catheter body diameter, wherein at least an initial refolding lumen of the refolding tool has an initial refolding lumen diameter that exceeds the specified refolded diameter and is sized to accommodate advancement of the balloon through the initial refolding lumen to refold the balloon to an initial refolded balloon diameter exceeding the specified refolded diameter and a final refolding lumen of the refolding tool has a final refolding lumen diameter that is smaller in diameter than the initial refolding lumen diameter and is sized to refold the initial refolded balloon diameter to the specified refolded diameter upon advancement of the balloon through the final refolding lumen to refold the balloon to substantially the specified refolded diameter.

2. The tool of claim 1, wherein the refolding tool body has at least one intermediate refolding lumen that has an intermediate refolding lumen diameter that is sized intermediate the initial and final refolding diameters to refold the initial refolded balloon diameter to the intermediate refolded diameter upon advancement of the balloon through the intermediate refolding lumen.

3. The tool of claim 2, wherein the refolding tool body has a first tool end surface and a plurality of second tool end surfaces spaced from said first tool end surface and the like plurality of refolding lumens each extend from the first tool end surface to a respective one of the second tool end surfaces so that each refolding lumen has a unique refolding lumen length that accommodates advancement of the catheter body through each refolding lumen and withdrawal of the balloon catheter back through the refolding lumen.

4. The tool of claim 3, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated wherein;

the refolding lumen diameters of each of the refolding lumens are increased to an enlarged second lumen end opening diameter at each of the second tool surfaces and define a funnel shaped insertion surface for contacting and guiding the distal balloon portion into the refolding lumen upon insertion of the balloon catheter distal segment into an enlarged first end opening and advancement through the refolding lumen.

5. The tool of claim 4, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

6. The tool of claim 2, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of the second tool surfaces and define a funnel shaped insertion surface for contacting and guiding the distal balloon portion into the refolding lumen upon insertion of the balloon catheter distal segment into an enlarged first end opening and advancement through the refolding lumen.

7. The tool of claim 6, wherein the refolding lumen diameters of each of the refolding lumens are increased to an enlarged first lumen end opening in a first tool surface and define a funnel shaped withdrawal surface for contacting and guiding the proximal balloon portion into the refolding lumen upon withdrawal of the balloon catheter distal segment through the refolding lumen and out of the enlarged second end opening.

8. The tool of claim 1, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of the second tool surfaces and define a funnel shaped insertion surface for contacting and guiding the distal balloon portion into the refolding lumen upon insertion of the balloon catheter distal segment into an enlarged first end opening and advancement through the refolding lumen.

9. The tool of claim 1, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

10. A refolding system for refolding a balloon of a balloon catheter of the type having an elongated catheter body having a catheter body diameter and enclosing a balloon catheter lumen extending distally from a distal lumen end opening having a distal lumen end opening diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising:

support means adapted to be assembled as an assembly with said catheter body for supporting the catheter body lumen in at least the balloon catheter distal segment of the catheter body from collapse when force is applied thereto; and a refolding tool having a plurality of refolding lumens extending therethrough having differing refolding lumen diameters, wherein at least an initial refolding lumen of the refolding tool has an initial refolding lumen diameter that exceeds the specified refolded diameter and is sized to accommodate advancement of the assembly of the support means and the balloon through the initial refolding lumen to refold the balloon to an initial refolded balloon diameter exceeding the specified refolded diameter, and a final refolding lumen of the refolding tool has a final refolding lumen diameter that is smaller in diameter than the initial refolding lumen diameter and is sized to refold the initial refolded balloon diameter to the substantially the specified refolded diameter upon advancement of the assembly of the support means and the catheter body distal segment through the final refolding lumen to refold the balloon to substantially the specified refolded diameter.

11. The system of claim 10, wherein the refolding tool body has at least one intermediate refolding lumen that has an intermediate refolding lumen diameter that is sized intermediate the initial and final refolding diameters to refold the initial refolded balloon diameter to the intermediate refolded diameter upon advancement of the assembly of the support means and the balloon catheter distal segment through the intermediate refolding lumen.

12. The system of claim 11, wherein the refolding tool body has a first tool end surface and a plurality of second tool end surfaces spaced from said first tool end surface and the like plurality of refolding lumens each extend from the first tool end surface to a respective one of the second tool end surfaces so that each refolding lumen has a unique refolding lumen length that accommodates advancement of the catheter body through each refolding lumen and withdrawal of the balloon catheter back through the refolding lumen.

13. The system claim 12, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of the second tool surfaces and define a funnel shaped insertion surface for contacting and guiding the distal balloon portion into the refolding lumen upon insertion of the balloon catheter distal segment into an enlarged first end opening and advancement through the refolding lumen.

14. The system of claim 13, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

15. The system claim 11, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of second tool surfaces and define a funnel shaped insertion surface for contacting and guiding the distal balloon portion into the refolding lumen upon insertion of the balloon catheter distal segment into an enlarged first end opening and advancement through the refolding lumen.

16. The system of claim 15, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

17. The system of claim 10, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of second tool surfaces and define a funnel shaped insertion surface for contacting and guiding the distal balloon portion into the refolding lumen upon insertion of the balloon catheter distal segment into an enlarged first end opening and advancement through the refolding lumen.

18. The system of claim 17, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

19. A refolding system for refolding a balloon of a balloon catheter of the type having an elongated catheter body having a catheter body diameter and enclosing a balloon catheter lumen extending distally from a distal lumen end opening having a distal lumen end opening diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising:

a support stylet having a stylet distal end and a stylet proximal end and a stylet length that exceeds the predetermined balloon length and a ball tip with a ball tip shape and diameter exceeding the distal lumen end opening diameter at the distal stylet end thereof adapted to be inserted into the distal lumen end opening and advanced proximally until the ball tip bears against but does not enter the distal lumen end opening or expand the distal lumen end opening diameter and the stylet extends within the balloon catheter lumen to the stylet proximal end at a location within the balloon catheter lumen proximal to the balloon, whereby the catheter body can be manually grasped at a supported location of the catheter body that the inserted stylet extends to and is proximal to the balloon; and a refolding tool having a plurality of refolding lumens extending therethrough having differing refolding lumen diameters, wherein at least an initial refolding lumen of the refolding tool has an initial refolding lumen diameter that exceeds the specified refolded diameter and is sized to accommodate advancement of the assembly of the support stylet and the balloon through the initial refolding lumen to refold the balloon to an initial refolded balloon diameter exceeding the specified refolded diameter, and a final refolding lumen of the refolding tool has a final refolding lumen diameter that is smaller in diameter than the initial refolding lumen diameter and is sized to refold the initial refolded balloon diameter to the substantially the specified refolded diameter upon advancement of the assembly of the support stylet and the balloon catheter distal segment through the final refolding lumen to refold the balloon to substantially the specified refolded diameter.

20. The system of claim 19, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of second tool surfaces and define a funnel shaped insertion surface for contacting and guiding the distal balloon portion into the refolding lumen upon insertion of the balloon catheter distal segment into an enlarged first end opening and advancement through the refolding lumen.

21. The system of claim 20, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

22. The system of claim 19, wherein the refolding tool body has at least one intermediate refolding lumen that has an intermediate refolding lumen diameter that is sized intermediate the initial and final refolding diameters to refold the initial refolded balloon diameter to the intermediate refolded diameter upon advancement of the assembly of the support stylet and the balloon catheter distal segment through the intermediate refolding lumen.

23. The system of claim 22, wherein the refolding tool body has a first tool end surface and a plurality of second tool end surfaces spaced from said first tool end surface and the like plurality of refolding lumens each extend from the first tool end surface to a respective one of the second tool end surfaces so that each refolding lumen has a unique refolding lumen length that accommodates advancement of the catheter body through each refolding lumen and withdrawal of the balloon catheter back through the refolding lumen.

24. The system of claim 23, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of the second tool surfaces and define a funnel shaped insertion surface for contacting and guiding the distal balloon portion into the refolding lumen upon insertion of the balloon catheter distal segment into the enlarged first end opening and advancement through the refolding lumen.

25. The system of claim 24, wherein the refolding lumen diameters of each of the refolding lumens are increased to an enlarged first lumen end opening in the first tool surface and define a funnel shaped withdrawal surface for contacting and guiding the proximal balloon portion into the refolding lumen upon withdrawal of the balloon catheter distal segment through the refolding lumen and out of the enlarged second end opening.

26. The system of claim 22, wherein the balloon mounted to the catheter body extends outward of the catheter body in the distal segment thereof and has a proximal balloon portion that increases in diameter distally when inflated, an intermediate balloon portion that is substantially cylindrical when inflated, and a distal balloon portion that decreases in diameter distally when inflated and wherein:

the refolding lumen diameters of each of the refolding lumens are increased to an enlarged second lumen end opening diameter at each of second tool surfaces and define a funnel shaped insertion surface for contacting and guiding the distal balloon portion into the refolding lumen upon insertion of the balloon catheter distal segment into an enlarged first end opening and advancement through the refolding lumen.

27. The system of claim 26, wherein the refolding lumen diameters of each of the refolding lumens are increased to an enlarged first lumen end opening in a first tool surface and define a funnel shaped withdrawal surface for contacting and guiding the proximal balloon portion into the refolding lumen upon withdrawal of the balloon catheter distal segment through the refolding lumen and out of the enlarged second end opening.

28. A method of refolding the flaps of a deflated balloon of a balloon catheter employing a refolding system the type set forth in claims 19, 20 or 21 from a deflated condition following an earlier inflation into a specified refolded diameter correlated with the catheter body diameter and sufficient to be advanced through a patient's vascular system by itself or within a guide catheter lumen to a desired vascular site comprising the steps of:

inserting the proximal stylet end of the support stylet into the distal lumen end opening so that the ball tip bears against but does not enter the distal lumen end opening or expand the distal lumen end opening diameter and the stylet extends within the balloon catheter lumen to the proximal stylet end at a location proximal to the balloon to stiffen and support the distal segment of the catheter body;

manually grasping the catheter body at the location that the inserted stylet extends to proximal to the balloon;

inserting the stylet ball tip into the initial refolding lumen of the refolding tool that exceeds the specified refolded diameter and the stylet ball tip diameter;

advancing and withdrawing the assembly of the support stylet and balloon catheter distal segment through the initial selected refolding lumen, whereby the flaps of the balloon are refolded to an initial refolded balloon diameter exceeding the specified refolded diameter;

positioning the stylet ball tip into the final refolding lumen of the refolding tool to refold the initial refolded balloon diameter to the specified refolded diameter; and advancing and withdrawing the assembly of the support stylet and balloon catheter distal segment through the final refolding lumen, whereby the flaps of the balloon are refolded to the specified refolded diameter.

29. A method of refolding the flaps of a deflated balloon of a balloon catheter employing a refolding system the type set forth in claims 22, 23, 24, 25, 26, or 27 from a deflated condition following an earlier inflation into a specified refolded diameter correlated with the catheter body diameter and sufficient to be advanced through a patient's vascular system by itself or within a guide catheter lumen to a desired vascular site comprising the steps of:

inserting the proximal stylet end of the support stylet into the distal lumen end opening so that the ball tip bears against but does not enter the distal lumen end opening or expand the distal lumen end opening diameter and the stylet extends within the balloon catheter lumen to the proximal stylet end at a location proximal to the balloon to stiffen and support the distal segment of the catheter body;

manually grasping the catheter body at the location that the inserted stylet extends to proximal to the balloon;

inserting the stylet ball tip into the initial refolding lumen of the refolding tool that exceeds the specified refolded diameter and the stylet ball tip diameter;

advancing and withdrawing the assembly of the support stylet and balloon catheter distal segment through the initial selected refolding lumen, whereby the flaps of the balloon are refolded to an initial refolded balloon diameter exceeding the specified refolded diameter;

advancing and withdrawing the assembly of the support stylet and balloon catheter distal segment through the intermediate selected refolding lumen, whereby the flaps of the balloon are refolded to an intermediate refolded balloon diameter exceeding the specified refolded diameter;

inserting the stylet ball tip into the final refolding lumen of the refolding tool to refold the initial refolded balloon diameter to the specified refolded diameter; and advancing and withdrawing the assembly of the support stylet and balloon catheter distal segment through the final refolding lumen, whereby the flaps of the balloon are refolded to the specified refolded diameter.

30. A method of refolding the flaps of a deflated balloon of a balloon catheter of the type having an elongated catheter body having a catheter body diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising the steps of:

selecting an initial refolding lumen of a refolding tool comprising a plurality of refolding lumens of differing refolding lumen diameters, wherein the initial selected refolding lumen is selected to exceed the specified refolded diameter;

manually grasping the catheter body proximal to the balloon;

inserting the balloon catheter body distal end into the selected initial refolding lumen;

advancing the balloon through the initial selected refolding lumen, whereby the balloon flaps are refolded to an initial refolded balloon diameter exceeding the specified refolded diameter;

inserting the folded balloon flaps of the balloon catheter body distal end into a further selected refolding lumen of the refolding tool that is smaller in diameter than the initial selected refolding lumen and greater in diameter than the catheter body diameter and is selected to refold the initial refolded balloon diameter to the specified refolded diameter; and advancing an assembly of a stylet ball tip and the balloon through the further selected refolding lumen whereby the balloon flaps are refolded to the specified refolded diameter.

31. The refolding method of claim 30, wherein the supporting step further comprises the steps of:

providing a support stylet having a stylet length that exceeds the predetermined balloon length and a ball tip with a ball tip shape and diameter exceeding the distal lumen end opening diameter at the distal stylet end thereof; and inserting a proximal stylet end of said support stylet into the distal lumen end opening so that the ball tip bears against but does not enter the distal lumen end opening or expand the distal lumen end opening diameter and the stylet extends within the balloon catheter lumen to the proximal stylet end to a location proximal to the balloon to stiffen and support the distal segment of the catheter body that is grasped and advanced.

32. The refolding method of claim 31, wherein the supporting step further comprises the steps of:

providing a support stylet having a stylet length that exceeds the predetermined balloon length and a ball tip with a ball tip shape and diameter exceeding the distal lumen end opening diameter at the distal stylet end thereof; and inserting the proximal stylet end of a support stylet into the distal lumen end opening so that the ball tip bears against but does not enter the distal lumen end opening or expand the distal lumen end opening diameter and the stylet extends within the balloon catheter lumen to the proximal stylet end to a location proximal to the balloon to stiffen and support the distal segment of the catheter body that is grasped and advanced.

33. The refolding method of claim 32, wherein the inserting and advancing steps further comprise the steps of:

inserting the stylet ball tip into the initial refolding lumen of the refolding tool that exceeds the specified refolded diameter and the stylet ball tip diameter;

advancing and withdrawing the assembly of the support stylet and balloon catheter distal segment through the initial selected refolding lumen, whereby the flaps of the balloon are refolded to an initial refolded balloon diameter exceeding the specified refolded diameter;

inserting the stylet ball tip into the intermediate refolding lumen of the refolding tool that exceeds the specified refolded diameter and the stylet ball tip diameter;

advancing and withdrawing the assembly of the support stylet and balloon catheter distal segment through the intermediate selected refolding lumen, whereby the flaps of the balloon are refolded to an intermediate refolded balloon diameter exceeding the specified refolded diameter;

inserting the stylet ball tip into the final refolding lumen of the refolding tool to refold the initial refolded balloon diameter to the specified refolded diameter; and advancing and withdrawing the assembly of the support stylet and balloon catheter distal segment through the final refolding lumen, whereby the flaps of the balloon are refolded to the specified refolded diameter.

34. A method of refolding the flaps of a deflated balloon of a balloon catheter of the type having an elongated catheter body having a catheter body diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising the steps of:

selecting an initial refolding lumen of a refolding tool comprising a plurality of refolding lumens of differing refolding lumen diameters, wherein the initial selected refolding lumen exceeds the specified refolded diameter;

manually grasping the catheter body proximal to the balloon;

inserting the balloon catheter body distal end into the selected initial refolding lumen;

advancing the balloon through the initial refolding lumen, whereby the balloon flaps are refolded to an initial refolded balloon diameter exceeding the specified refolded diameter;

inserting the initially folded flaps of the balloon catheter body distal end into an intermediate refolding lumen of the refolding tool that is smaller in diameter than the initial refolding lumen and greater in diameter than the catheter body diameter and is selected to refold the initial refolded balloon diameter to an intermediate refolded diameter greater than the specified refolded diameter;

advancing the assembly of the stylet ball tip and the balloon through the intermediate refolding lumen whereby the balloon flaps are refolded to the intermediate refolded diameter;

inserting the intermediate folded flaps of the balloon catheter body distal end into a further selected refolding lumen of the refolding tool that is smaller in diameter than the initial selected refolding lumen and greater in diameter than catheter body diameter and is selected to refold the initial refolded balloon diameter to the specified refolded diameter; and advancing the assembly of the stylet ball tip and the balloon through the final refolding lumen, whereby the balloon flaps are refolded to the specified refolded diameter.

35. A method of refolding a balloon of a balloon catheter of the type having an elongated catheter body having a catheter body diameter and enclosing a balloon catheter lumen extending distally from a distal lumen end opening having a distal lumen end opening diameter and an inflatable and deflatable balloon of a predetermined balloon length mounted to a distal segment of the catheter body from a deflated condition following an earlier inflation into a specified refolded diameter correlated with the catheter body diameter and sufficient to be advanced through a patient's vascular system by itself or within a guide catheter lumen to a desired vascular site comprising the steps of:

inserting a proximal stylet end of a support stylet having stylet length that exceeds the predetermined balloon length and a ball tip with a ball tip shape and diameter exceeding the distal lumen end opening diameter at a distal stylet end thereof into the distal lumen end opening so that the ball tip bears against but does not enter the distal lumen end opening or expand the distal lumen end opening diameter and the support stylet extends within the balloon catheter lumen to the proximal stylet end to a location proximal to the balloon to stiffen and support the distal segment of the catheter body;

selecting an initial refolding lumen of a refolding tool comprising a plurality of refolding lumens of differing refolding lumen diameters, wherein the initial selected refolding lumen diameters, wherein the initial selected refolding lumen is selected to exceed the specified refolded diameter and the stylet ball tip diameter;

manually grasping the catheter body at the location that the inserted stylet extends to proximal to the balloon;

inserting the stylet ball tip into the selected initial refolding lumen;

advancing the assembly of the stylet ball tip and the balloon through the initial selected refolding lumen;

withdrawing the advanced assembly of the stylet ball tip and the balloon through the initial selected refolding lumen whereby the balloon is refolded to an initial refolded balloon diameter exceeding the specified refolded diameter;

positioning the stylet ball tip into a further selected refolding lumen of the refolding tool that is smaller in diameter than the initial selected refolding lumen and greater in diameter than the stylet ball tip diameter and is selected to refold the initial refolded balloon diameter to the specified refolded diameter;

advancing the assembly of the stylet ball tip and the balloon through the further selected refolding lumen; and withdrawing the advanced assembly of the stylet ball tip and the balloon through the further selected refolding lumen whereby the balloon is refolded to the specified refolded diameter.

* * * * *